US010690918B2

United States Patent
Inman et al.

(10) Patent No.: US 10,690,918 B2
(45) Date of Patent: Jun. 23, 2020

(54) OPTICAL HEAD-MOUNTED DISPLAYS FOR LASER SAFETY EYEWEAR

(71) Applicant: U.S.A., AS REPRESENTED BY THE ADMINISTRATOR OF NASA, Washington, DC (US)

(72) Inventors: Jennifer A. Inman, Williamsburg, VA (US); Paul M. Danehy, Newport News, VA (US); Brian K. Perkins, Newport News, VA (US); Christopher J. Peters, Olivette, MO (US)

(73) Assignee: UNITED STATES OF AMERICA AS REPRESENTED BY THE ADMINISTRATOR OF NASA, Washington, DC (US)

( * ) Notice: Subject to any disclaimer, the term of this patent is extended or adjusted under 35 U.S.C. 154(b) by 62 days.

(21) Appl. No.: 15/832,372

(22) Filed: Dec. 5, 2017

(65) Prior Publication Data

US 2018/0172996 A1 Jun. 21, 2018

Related U.S. Application Data

(60) Provisional application No. 62/436,004, filed on Dec. 19, 2016.

(51) Int. Cl.
*G02B 27/01* (2006.01)
*G02C 7/10* (2006.01)
(Continued)

(52) U.S. Cl.
CPC .......... *G02B 27/0172* (2013.01); *A61F 9/022* (2013.01); *G02B 27/017* (2013.01);
(Continued)

(58) Field of Classification Search
CPC .............. G02B 27/0172; G02B 27/017; G02B 2027/0138; G02B 2027/0178;
(Continued)

(56) References Cited

U.S. PATENT DOCUMENTS

| 4,867,551 A | 9/1989 | Perera |
| 5,175,571 A | 12/1992 | Tanefsky et al. |

(Continued)

FOREIGN PATENT DOCUMENTS

| CN | 1335529 A | 2/2002 |
| CN | 1957284 A | 5/2007 |

(Continued)

OTHER PUBLICATIONS

Laser viewing cards, retrieved from https://www.thorlabs.com/NewGroupPage.cfm?ObjectGroup_ID=296, Accessed on May 5, 2017.

(Continued)

*Primary Examiner* — Brent D Castiaux
(74) *Attorney, Agent, or Firm* — M. Bruce Harper; Jonathan B. Soike; Robin W. Edwards

(57) ABSTRACT

According to certain examples, a head-mounted apparatus includes a safety eyewear component and an optical display coupled to the safety eyewear component. The safety eyewear component is configured to be worn of a head of an operator and to block transmission of a laser light therethrough. The optical display is configured to receive data associated with the laser light and to display a visual representation of the laser light in a field of view of the operator. In other examples, an apparatus includes a display, a sensor, at least one processor and at least one memory storing computer-readable instructions that, when executed by the at least one processor, cause the apparatus to receive, from the sensor, data associated with a laser light, process (Continued)

the data, and provide an image to the display, such as a representation of the laser light.

14 Claims, 5 Drawing Sheets

(51) Int. Cl.
*G06T 19/00* (2011.01)
*A61F 9/02* (2006.01)
*G02B 5/20* (2006.01)

(52) U.S. Cl.
CPC ............ *G02C 7/104* (2013.01); *G06T 19/006* (2013.01); *G02B 5/20* (2013.01); *G02B 5/208* (2013.01); *G02B 2027/014* (2013.01); *G02B 2027/0138* (2013.01); *G02B 2027/0141* (2013.01); *G02B 2027/0147* (2013.01); *G02B 2027/0178* (2013.01)

(58) Field of Classification Search
CPC .... G02B 2027/0141; G02B 2027/0147; G02B 2027/014; G02B 5/208; G02B 5/20; G02C 7/104; G06T 19/006; A61F 9/022
See application file for complete search history.

(56) References Cited

U.S. PATENT DOCUMENTS

| | | | |
|---|---|---|---|
| 6,034,653 A | 3/2000 | Robertson et al. | |
| 6,356,392 B1 | 3/2002 | Spitzer | |
| 6,879,443 B2 | 4/2005 | Spitzer et al. | |
| 7,158,096 B1 | 1/2007 | Spitzer | |
| 7,631,968 B1 | 12/2009 | Dobson et al. | |
| 7,648,236 B1 | 1/2010 | Dobson | |
| 7,663,805 B2 | 2/2010 | Zaloum et al. | |
| 7,675,683 B2 | 3/2010 | Dobson et al. | |
| 7,843,403 B2 | 11/2010 | Spitzer | |
| 8,000,000 B2 | 8/2011 | Greenberg et al. | |
| 9,285,592 B2 | 3/2016 | Olsson et al. | |
| 2003/0090439 A1 | 5/2003 | Spitzer et al. | |
| 2004/0252077 A1 | 12/2004 | Terasak | |
| 2005/0083591 A1 | 4/2005 | Kobayashi et al. | |
| 2005/0219152 A1 | 10/2005 | Budd et al. | |
| 2006/0017882 A1 | 1/2006 | Hiramoto | |
| 2007/0008484 A1 | 1/2007 | Jannard | |
| 2008/0291277 A1 | 11/2008 | Jacobsen et al. | |
| 2009/0201460 A1 | 8/2009 | Blum et al. | |
| 2010/0045928 A1 | 2/2010 | Levy | |
| 2010/0073262 A1 | 3/2010 | Matsumoto | |
| 2010/0079356 A1 | 4/2010 | Hoellwarth | |
| 2010/0110368 A1 | 5/2010 | Chaum | |
| 2010/0149073 A1 | 6/2010 | Chaum | |
| 2010/0157433 A1 | 6/2010 | Mukawa et al. | |
| 2010/0188314 A1 | 7/2010 | Miyake et al. | |
| 2011/0012814 A1 | 1/2011 | Tanaka | |
| 2011/0213664 A1* | 9/2011 | Osterhout | G02B 27/017 705/14.58 |
| 2011/0248905 A1 | 10/2011 | Chosokabe et al. | |
| 2013/0016070 A1* | 1/2013 | Starner | G02B 27/017 345/175 |
| 2014/0160162 A1* | 6/2014 | Balachandreswaran | G03B 17/54 345/633 |
| 2014/0180826 A1* | 6/2014 | Boal | G06Q 20/209 705/14.66 |
| 2016/0349539 A1* | 12/2016 | Waisman | G02C 11/10 |
| 2018/0095607 A1* | 4/2018 | Proctor | G09F 19/18 |

FOREIGN PATENT DOCUMENTS

| | | |
|---|---|---|
| CN | 101467446 A | 6/2009 |
| CN | 101675371 A | 3/2010 |
| CN | 101846802 A | 9/2010 |
| CN | 101930125 A | 12/2010 |
| EP | 0899599 A2 | 3/1999 |
| WO | 2010092904 A1 | 8/2010 |

OTHER PUBLICATIONS

Certified Laser Safety Glasses, retrieved from http://www.thorlabs.com/newgrouppage9.cfm?objectgroup_ID=762, Accessed on May 5, 2017.

Laser Detection Products, retrieved from http://www.edmundoptics.com/lasers/laser-measurements/infrared-ir-ultraviolet-uv-viewers/aser-detection-products/1613, Accessed on May 5, 2017.

Near Infrared (NIR) Sensor Cards retrieved from http://www.newport.com/Infared-and-Ultraviolet-Sensor-Cards/139709/1033/infor.aspx, Accessed on May 5, 2017.

View-It IR Detectors retrieved from http://www.kenteklaserstore.com/view-it-ir-detectors.aspx, Accessed on May 5, 2017.

* cited by examiner

OPTICAL HEAD-MOUNTED DISPLAYS FOR LASER SAFETY EYEWEAR

CROSS-REFERENCE TO RELATED PATENT APPLICATION(S)

This patent application claims the benefit of and priority to U.S. Provisional Application No. 62/436,004, filed on Dec. 19, 2016, the contents of which are hereby incorporated by reference in their entirety.

STATEMENT REGARDING FEDERALLY SPONSORED RESEARCH OR DEVELOPMENT

The invention described herein was made in part by employees of the United States Government and may be manufactured and used by and for the Government of the United States for governmental purposes without the payment of any royalties thereon or therefore.

BACKGROUND

Aspects of this disclosure generally relate to systems and methods for laser alignment and laser safety eyewear.

Safe operation of a laser beam apparatuses includes proper eyewear protection. Known laser eyewear protection may provide a physical and/or optical barrier to protect the eyes of laser operators by preventing transmission of light at the laser's wavelength. Such laser eyewear protection is thus rated for the specific wavelength, power, and/or pulse characteristics of the laser being operated.

In order to align a laser (e.g., with a power meter, an iris, an optic, and the like) for certain procedures, an operator may need to be able to see light of the laser that is reflected or scattered (e.g., by particles in air or objects in the path of the laser). Ideally, a laser operator would only make adjustments to the laser's path with the laser operating at the lowest possible power setting. However, known laser eyewear protection, e.g., laser goggles, often prevents the laser light from being seen, especially at lower power settings.

To compensate for the above shortcomings in laser eyewear protection, laser viewing cards may be employed in conjunction with laser goggles. Such laser viewing cards emit broadband fluorescence that can be seen through laser goggles. Thus, the laser beam location may be viewed by placing the viewing card in the path of the laser beam.

However, known laser viewing cards often have a fairly high energy threshold that must be met before sufficient fluorescence to see the laser beam on the card is emitted. Such a high energy threshold may thus require the laser to be operated at a higher power setting than the threshold lasing power. Higher power is generally more hazardous for both equipment and personnel and can result in damage to optics or other equipment (including the viewing card itself) if the beam is misaligned.

Remote viewing of a laser may also be accomplished using fixed or hand-held video cameras, cell-phone cameras, or a separate monitor or display. However, video cameras are often cumbersome to use and require additional space for the extra equipment, alignment (in the case of fixed cameras), and a free hand (in the case of hand-held cameras). Monitors may not always be placed in a convenient location, i.e., where visible by the operator making adjustments to optical components like mirrors and lenses.

Prior art solutions for laser safety and alignment systems have not resolved the need for an approach to perform the above functions with accuracy, efficiency, or with cross-applicability to many various system architectures. Therefore, there is a need for systems and methods that address one or more of the deficiencies described above.

SUMMARY

The present disclosure relates to head-mounted apparatuses, systems and methods that that allow a laser operator to safely view laser light and experimental equipment while using high-powered lasers. Such apparatuses, systems and methods allow for alignment of a laser beam even at low power setting and without requiring cumbersome camera or image monitoring equipment.

Various aspects of the present disclosure relate to head-mounted apparatus that provide laser eye protection and real-time display indicating a representation of a laser. Aspects of the present disclosure also include methods of operating a head-mounted apparatus to align a laser beam.

In one embodiment, a head-mounted apparatus includes a safety eyewear component and an optical display coupled to the safety eyewear component. The safety eyewear component may be configured to be worn on the head of an operator and to block transmission of light from a laser therethrough. In some examples, the safety eyewear component may include a plurality of filters, each filter corresponding to a specified laser wavelength, wavelengths, or wavelength range.

The optical display may be configured to receive data associated with the light from a laser and display a visual representation of the laser in a field of view of the operator. For instance, the optical display may be configured to process the received data such that the visual representation depicts a path of the laser beam and/or may be configured to provide an augmented reality display (e.g., a picture-in-picture) in the field of view of the operator. The optical display may be configured to communicate with a remote computing system. The optical display may include one or more input devices configured to receive a user selection to modify a setting of the optical display and/or may be configured to provide optical zoom in the field of view of the operator. The optical display may be configured to provide graphical or textual information relating to a setting of the optical display. The optical display may be configured to receive input from one or more sensors, e.g., cameras and/or power meters.

In another embodiment, an apparatus includes a display, a sensor, at least one processor and at least one memory. The at least one memory may store computer-readable instructions that, when executed by the at least one processor, cause the apparatus to at least receive, from the sensor, data indicative of detected light from a laser (e.g., scattered or reflected), process the data, and provide an image to the display. The image provided to the display is generated based on the processed data and may include a representation of the laser beam. In some examples, the at least one memory may further store computer-readable instructions that, when executed by the at least one processor cause the apparatus to adjust a viewing position responsive to receiving a user selection to modify a viewing option.

The apparatus may further include a laser eye protection component and the apparatus may be a head-mounted apparatus. In such examples, a portion of the laser eye protection component and a portion of the display may be positioned to align with an eye region of a user. The image provided to the display may include a simulated projection of the laser beam that corresponds to an actual projection of the laser beam.

In yet another embodiment, a system includes a head-mounted frame, a safety lens module removably coupled to the head-mounted frame and configured to block transmission of laser light, and an optical display module removably coupled to the head-mounted frame and configured to provide a visualization corresponding to the laser. As used herein, the term "removably coupled" may refer to a physical coupling (e.g., fastening, bolting, interlocking, press fitting, or any of various other coupling methods) between two objects that allows the structures to be uncoupled by a user. The optical display module may be configured to provide an augmented reality display representing the laser beam. The optical display module may be configured to provide a plurality of user-selectable viewing options and/or an indication of: a power meter output of the laser beam and/or a beam profile intensity measurement. The safety lens module may include a plurality of removable lens inserts, each lens insert rated for a specific laser wavelength. In some examples, the safety lens module may be positioned outside of the optical display module when coupled to the head-mounted frame. In some other examples, the safety lens module may be positioned inside of the optical display module when coupled to the head-mounted frame. The head-mounted frame may be configured to be worn with: only the safety lens module, only the optical display module, or both the safety lens module and the optical display module.

These and other features, advantages, and objects of the present disclosure will be further understood and appreciated by those skilled in the art by reference to the following specifications, claims, and appended drawings.

BRIEF DESCRIPTION OF THE DRAWINGS

Various aspects and advantages of the disclosed embodiments will become apparent upon review of the following detailed description and upon reference to the drawings in which.

DETAILED DESCRIPTION OF THE INVENTION

Figure 1:
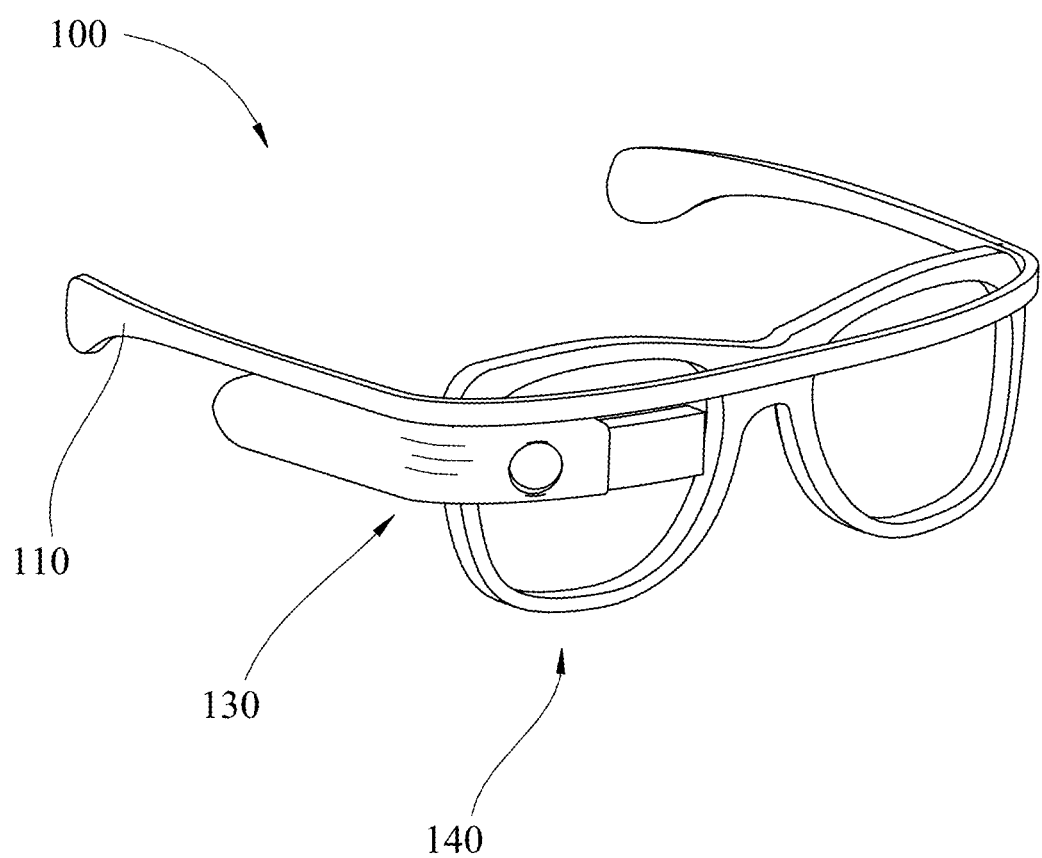
FIG. 1 illustrates a perspective view of an eyewear device in accordance with one or more aspects of the present disclosure.

For purposes of description herein, the terms "upper," "lower," "right," "left," "rear," "front," "vertical," "horizontal," and derivatives thereof shall relate to the invention as oriented in FIG. 1. However, it is to be understood that the disclosed embodiments may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

In the following description, reference is made to the accompanying drawings which show, by way of illustration, various example systems and environments in which aspects of the present disclosure may be practiced. It is to be understood that other specific arrangements of parts, example systems, and environments may be utilized and structural and functional modifications may be made without departing from the scope of this disclosure.

In addition, the present disclosure is described in connection with one or more embodiments. The descriptions set forth below, however, are not intended to be limited only to the embodiments described. To the contrary, it will be appreciated that there are numerous equivalents and variations that may be selectively employed that are consistent with and encompassed by the disclosures below.

Figure 2:
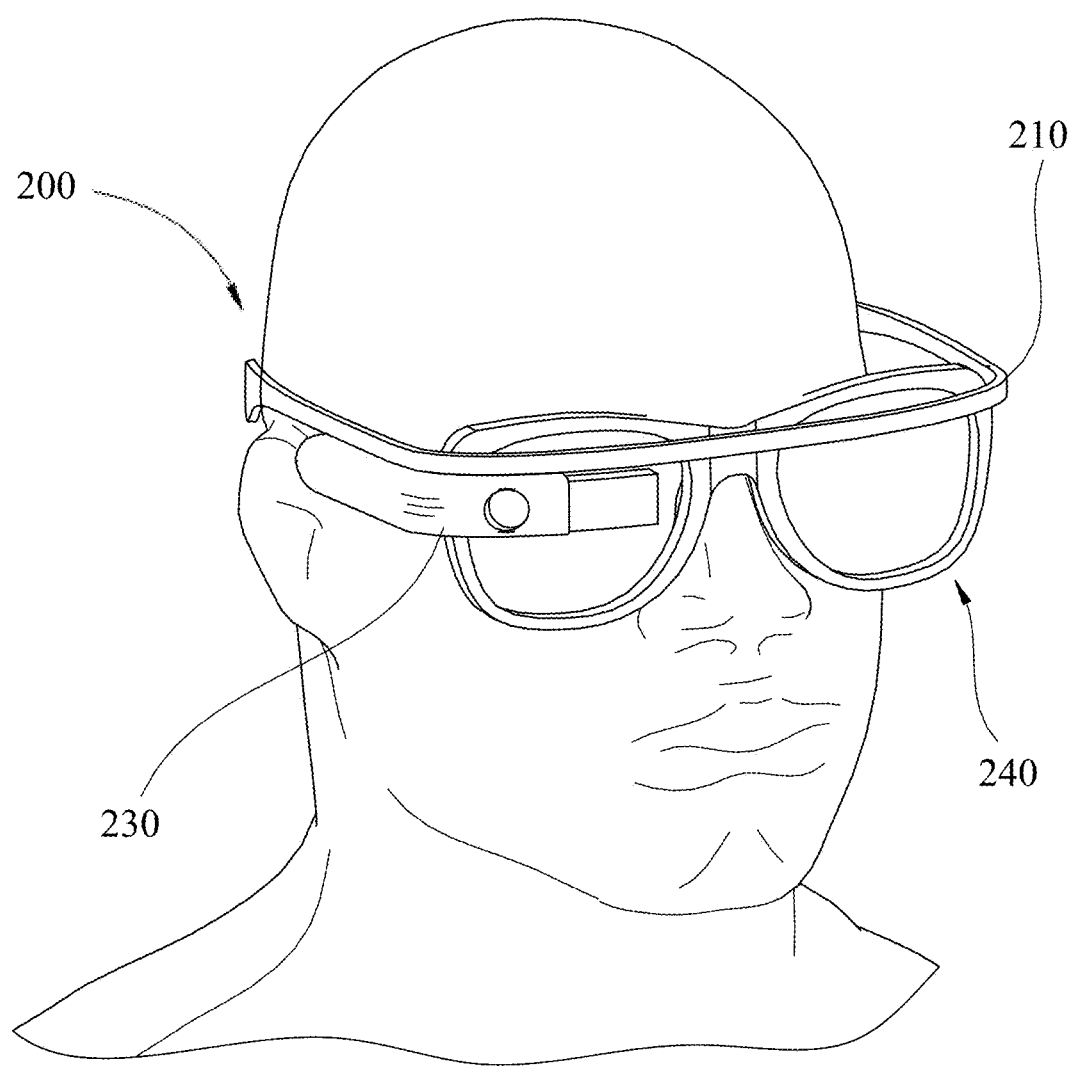
FIG. 2 illustrates a eyewear device worn on an operator in accordance with one or more aspects of the present disclosure.

As shown in FIG. 1, an eyewear device 100 in accordance with one or more aspects of the present disclosure may include an optical display 130 and a laser safety eyewear component 140. Optical display 130 and laser safety eyewear component 140 may each be coupled to a head-mounted frame or an adapter that connects to an existing head-mounted frame 110 such that eyewear device 100 can be worn on the head of an operator, e.g., with optical display 130 and laser safety eyewear component 140 substantially in front of the eyes of the operator, or with at least a portion of optical display 130 and at least a portion of laser safety eyewear component 140 in a field of view of the operator. For example, as shown in FIG. 2, an eyewear device 200 in accordance with one or more aspects of the present disclosure may be worn on a head of an operator. Eyewear device 200 may include a head-mounted frame or an adapter that connects to an existing head-mounted frame 210, an optical display 230 and a laser safety eyewear component 240, similar to eyewear device 100 FIG. 1. When eyewear device 200 is worn as shown in FIG. 2, laser safety eyewear component 240 substantially covers an eye area and optical display 230 is positioned to provide a display in at least a portion of the operator's field of view.

Referring again to FIG. 1, laser safety eyewear component 140 may be an optically opaque eyewear and may be configured to block transmission of light from a laser or other light that may be harmful to a human eye. Laser safety eyewear component 140 may include lens inserts, with various filters rated for a wavelength of the specific laser being operated. Such lens inserts may be removably mounted in the laser safety eyewear component 140. In some embodiments, laser safety eyewear component 140 may be an existing laser eyewear device, and optical display 130 is merely attached to the existing laser eyewear, e.g., using an adaptor.

Optical display 130 may provide a digital display to at least a portion of the eyewear device 100. The provided digital display may display a visual representation of light from the laser using a frequency range of light able to pass through the laser safety eyewear component 140. In this manner, an operator wearing the eyewear device 100 may be able to visualize light from a laser that is otherwise invisible due to the laser safety eyewear component 140 or due to the wavelength of the laser. In other words, eyewear device 100 may simplify laser alignment operation by allowing an operator wearing protective eyewear to see a representation of the laser beam and/or scattered and/or reflected laser light without the need for adjusting the intensity of the laser beam and/or additional laser viewing equipment. As described in more detail below, optical display 130 may provide an augmented reality display to the operator. For example, optical display 130 may provide a display with a visual representation of the laser beam depicted in the same spatial location as the actual laser beam within the eyewear field of view. Additionally or alternatively, optical display 130 may display, in a portion of the field of view, information such as laser setting information or may provide a selection of viewing options in which optical display 130 provides the visualization. Optical display 130 may additionally or alternatively display indicators of one or more characteristics of the laser beam including, for example, laser beam intensity, laser beam profile, an output from a power meter of the laser, or combinations thereof. In some embodiments, optical display 130 may be configured to provide an optical zoom to the display.

Eyewear devices in accordance with the present disclosure may enhance safety and reduce potential damage to other equipment because the laser beam performed with the laser operating at a low setting (i.e., the laser operator does not have to increase a power level of the laser beam to provide visibility of the laser beam). The optical display may provide the operator with real-time information. "Real time," as defined and used herein, means delayed only by transmission, reception, processing, and display. In other words, an image on the optical display may be provided during operation of the laser beam and may update as the laser is further moved for alignment.

Figure 3:
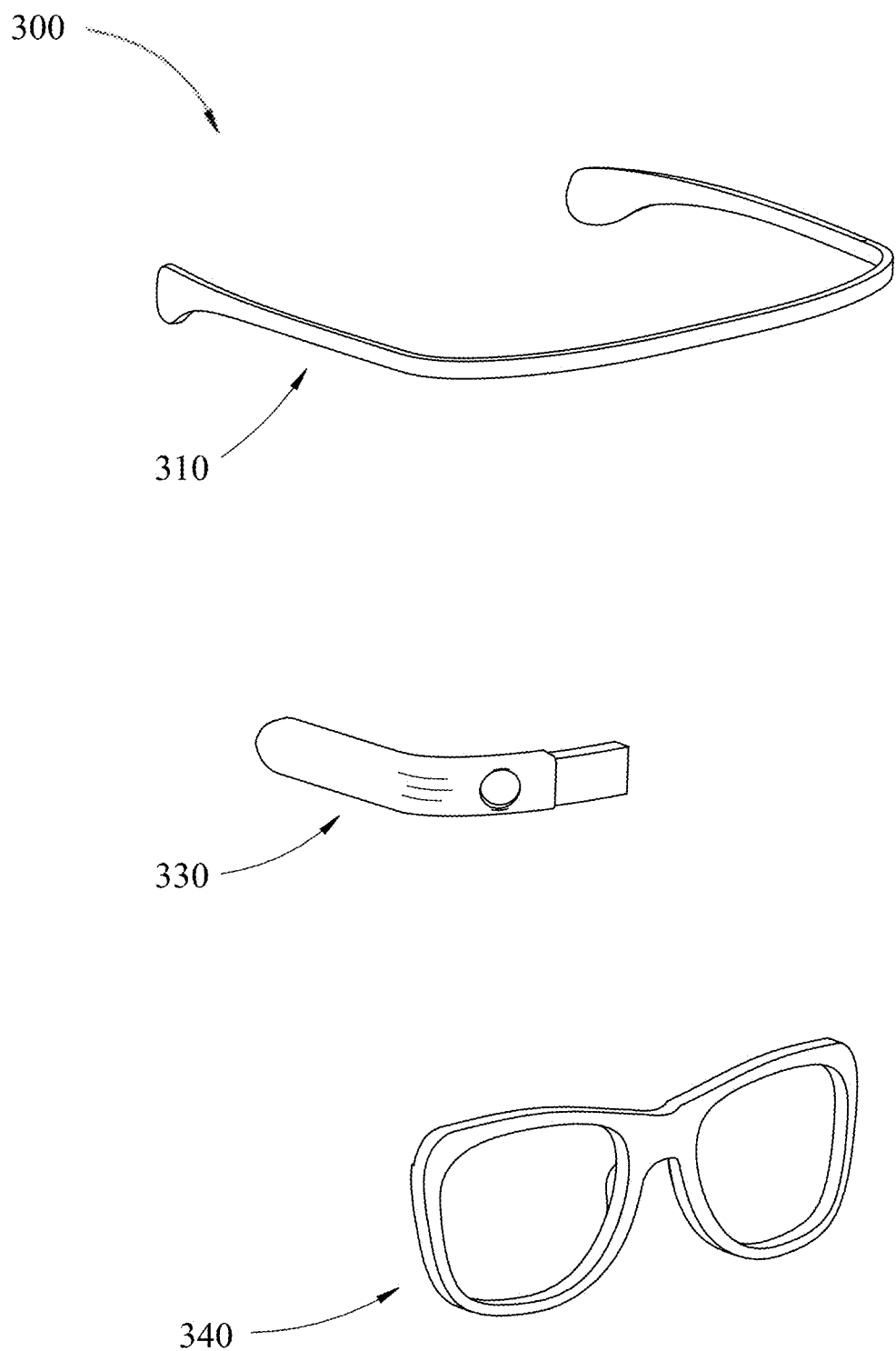
FIG. 3 illustrates an exploded view of an eyewear device in accordance with one or more aspects of the present disclosure.

As shown in the exploded view of FIG. 3, an eyewear device 300 in accordance with one or more aspects of the present disclosure may include a head-mounted frame or an adapter that connects to an existing head-mounted frame 310, an optical display 330 and a laser safety eyewear component 340, similar to eyewear devices 100 and 200 of FIGS. 1 and 2, respectively. Optical display 330 and/or laser safety eyewear component 340 may be removably mounted in head-mounted frame or frame adapter 310. In other words, eyewear device 300 may be reconfigured such that only the optical display 330 or only the laser safety eyewear component 340 is mounted on the head-mounted frame. For example, if a task does not require optical display 330, optical display 330 may be detached from eyewear device and a user may employ eyewear device 300 with only the laser safety eyewear component 340 mounted thereto. Similarly, laser safety eyewear component 340 may be removed and a user may employ eyewear device 300 with only optical display 330 mounted thereto.

When assembled, optical device 330 may be mounted on head-mounted frame or frame adapter 310 over laser safety eyewear component 340, e.g., similar to the configuration of eyewear devices 100 and 200 of FIGS. 1 and 2, respectively. However, in some examples, optical device 330 may be mounted on head-mounted frame or frame adapter 310 on an interior side of laser safety eyewear component 340, e.g., a side facing the operator's eyes. The location of the optical device 330 on head-mounted frame or frame adapter 310, i.e., relative to the operator's field of view, may be adjusted to various positions. For example, optical device 330 may be positioned below or above an approximate center of an operator's field of view. In some examples, optical device 330 may be positioned proximate to a right side, a left side, or a middle region.

Still in some examples, eyewear device 300 may include head-mounted frame or frame adapter 310 and optical display 330, without laser safety eyewear component 340. In such an example, an operator may wear an existing laser safety eyewear in conjunction with eyewear device 300. Additionally, optical display 330 may be configured to adjust display data based on the type of laser safety eyewear employed. In particular, eyewear device 300 without laser safety eyewear component 340 may be worn with existing laser goggles. The view through the existing laser goggles may be enhanced in some cases by converting the color being observed to another color that transmits through the goggles. For example, if a red laser is being used and red-blocking laser safety eyewear are worn, software associated with eyewear device 300 may convert red to blue, so as to be readily transmitted through the laser safety eyewear. Similarly, color video may be converted to black-and-white to transmit through the laser safety eyewear. Additional aspects of software associated with eyewear devices in accordance with the present disclosure are described in more detail below. A completely opaque laser safety eyewear may be worn with eyewear device 300 such that the laser operation is suitable for all wavelengths. Currently, there are many different types of eyewear associated with different types, powers, and colors of lasers. Head-mounted frame or frame adapter 310 may have many different manifestations, which allow eyewear device 300 to be compatible with these many different type of eyewear. Eyewear device 300 may thus be employed with any such types of eyewear.

Figure 4:
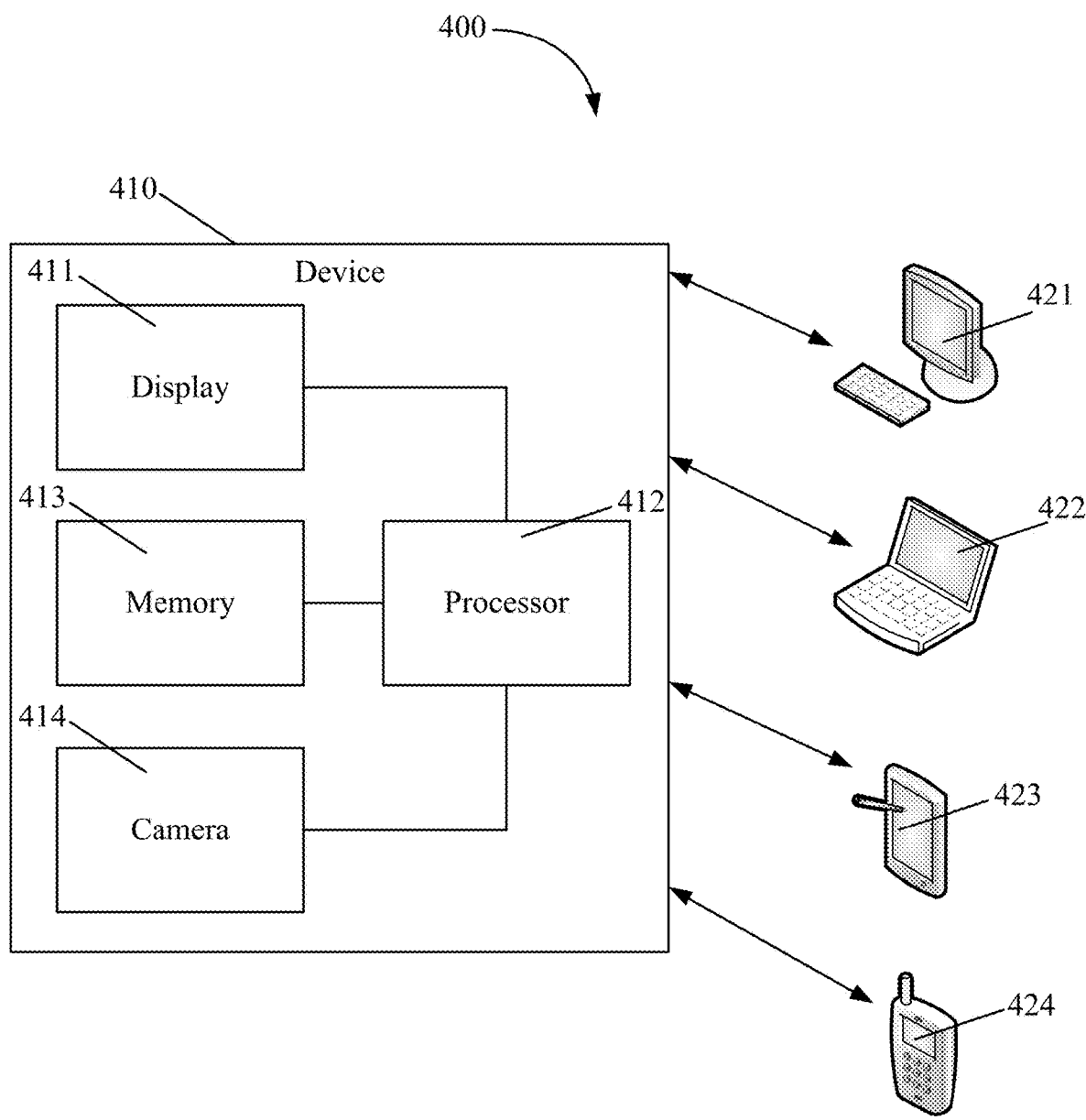
FIG. 4 schematically illustrates a laser alignment and visualization system in accordance with one or more aspects of the present disclosure.

FIG. 4 illustrates a laser alignment and visualization system employing eyewear devices in accordance with the present disclosure. In system 400, a device 410 may include display 411, processor 412, memory 413 and camera 414. Device 410 may be any type of device that can receive data and display information associated with the received data, such as the eyewear devices of FIGS. 1-3. Display 411 may include an optical display module that provides a visualization of a laser beam. Display 411 may provide image, video, textual and/or graphical information corresponding to received data, e.g., from camera 414.

Processor 412 may be coupled to the display 411, memory 413 and/or camera 414. For example, processor 412 may receive data from camera 414 and may process and/or configure data to be provided on display 411. Camera 414 may be integrated into optical display 330 or be a separate device or devices. Camera 414 may be sensitive to colors of invisible laser light that the human eye cannot detect. Accordingly, camera 414 may be used to align, for example, high powered infrared lasers like Nd:YAG lasers and for viewing the beam profiles during the alignment process. Additionally, camera 414 may also capture eye-safe invisible (e.g., infrared or ultraviolet) lasers. Processor 412 may execute a series of computer-readable instructions to display a visual representation of a laser beam on display 411, among other things.

Memory 413 may provide on-board data storage and may store software that can be executed by processor 412. For example, memory 413 may store software used by device 410 specific to visualizing a laser beam. Such software may include digital zoom, image stabilization, real-time image enhancement (e.g., using image subtraction to visualize the laser beam), real-time image processing, edge-detection, exposure time adjustment, line-fitting to visualize the laser beam's path in a laboratory environment, curve-fitting to extract a laser spatial profile as a laser is aligned, image capture, video capture, overlays from other laboratory equipment including power meters and oscilloscopes, and the like. Additionally, processes for augmentation of the display to include a graphical representation the laser may utilize various software processes including, for example, Google Glass Develop Kit (GDK), Open Source Computer Vision, Library (Open CV); Butterknife (Jake Wharton), Floating Action Button (Dmytro Tarianyk), Recon Jet Software Development Kit (Recon Jet), Vuzix Software Development Kit (Vuzix), and/or Circular Progress View (Rahat Ahmed).

Device 410 may also include one or more input devices (not pictured), including but not limited to a microphone, keypad, touch screen, or other such devices through which a user may provide input. Accordingly, the software stored by memory 413 may be controlled or executed through voice commands, gestures, and/or through computer user interface, depending on the input device includes with device 410. For example, upon powering up, device 410 may begin in a default mode. Upon receiving a user input selection on at least one of the input devices, a desired mode may subsequently be activated.

Device 410 may communicate with any number of remote devices such as computer system 421, laptop 422, tablet computing device 423, smartphone 424, or other such devices configured to send/receive data. Communication with device 410 and other remote devices may occur using various wired and/or a wireless communication protocols including, for example, Ethernet, PCIe, USB, Bluetooth, IEEE 802.11x, hiperLAN, CDMA, FDMA, TDMA, PCS, GSM, LTE, Near-field communications (NFC), Zigbee, Z-Wave, Thread, HDMI, and/or streaming protocols such as Google Cast, Dell Cast, and/or Apple AirPlay.

Eyewear devices in accordance with one or more embodiments of the present disclosure may offer many advantages over existing systems. For example, in some embodiments, an eyewear device may combine several tools needed for laser operations in a single system or apparatus. In particular, an optical head-mounted display module, real-time image processing, and laser safety eyewear may be integrating into a single device. The eyewear device also allows an operator to visualize light from a laser beam at lower power settings while still wearing laser safety eyewear. Accordingly, laser alignment can be performed at lower power settings, which is safer and more efficient. Additionally, the camera or other image or video recording device of the eyewear device may be sensitive to light outside the visible region of the spectrum, thus allowing otherwise invisible laser light to be visualized.

Figure 5:
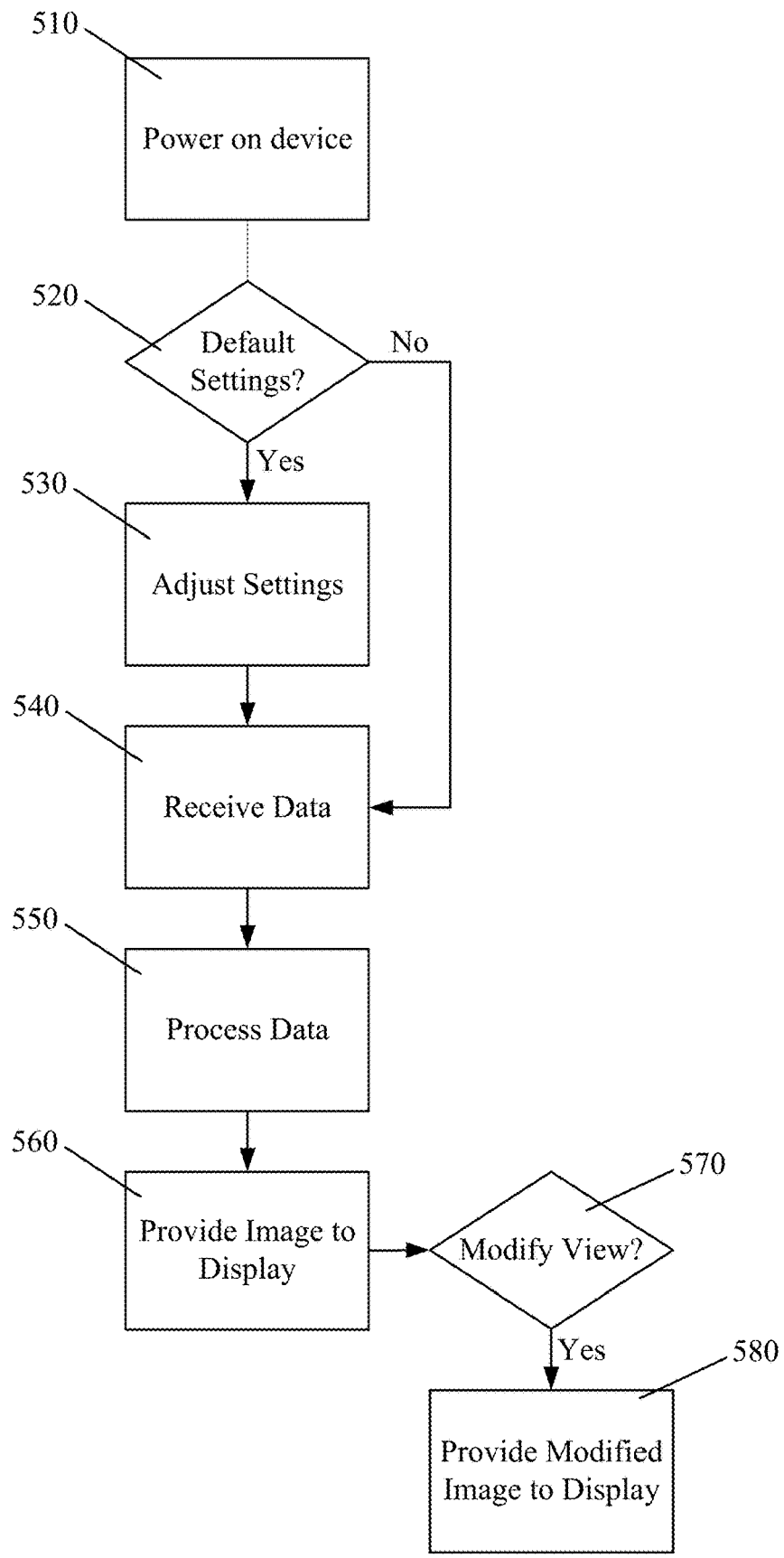
FIG. 5 is a flowchart describing a method for alignment and visualization of a laser in accordance with one or more aspects of the present disclosure.

FIG. 5 illustrates a flowchart describing a method of operating devices, apparatuses and systems as described herein. At step 510, the device is powered on. Upon powering on, the device will be set to a default setting. At step 520, the device may determine if the default setting is appropriate or if the setting should be adjusted at step 530, e.g., by prompting a user and/or by sensing certain settings of the laboratory environment. If the device determines that the default settings are not appropriate, at step 540, settings may be adjusted as appropriate. For example, certain settings may include a power level of the laser, a type of display to be provided, a viewing option to be provided and/or a type of laser eye protection being used.

After the settings are adjusted or upon determining that the default settings are appropriate, operation may commence. At step 540, the device may receive data, e.g., via a camera or other image recording device, associated with the laser light. At step 550, the received data are processed using any number of software features as described herein. At step 560, an image is provided to a display of the device in an operator's field of view, the image being based on the processed data from step 550. Throughout operation of the device, steps 540-560 may be repeated to provide ongoing and updated images to display, e.g., in real time. A user may select, during operation of the device, a change in input device, viewing output and/or display output. At step 570, the device may determine if the view in which the image is provided is to be modified, e.g., in response to a user selection. Accordingly, a modified image may be provided to display at step 580 in response to determining that the view is to be modified. After the modified image has been provided, steps 540-580 may be repeated throughout operation of the device and/or until the device is powered down.

While preferred embodiments and example configurations have been herein illustrated, shown and described, it is to be appreciated that various changes, rearrangements and modifications may be made therein, without departing from the scope of the invention as defined by the claims. It is intended that specific embodiments and configurations disclosed are illustrative of the preferred and best modes for practicing the invention, and should not be interpreted as limitations on the scope of the invention as defined by the appended claims and it is to be appreciated that various changes, rearrangements and modifications may be made therein, without departing from the scope of the invention.

Eyewear devices and systems in accordance with the present disclosure are not limited to operation of lasers. For example, the eyewear device may be suitable for use during welding operations.

While the invention has been described with respect to specific examples including presently preferred modes of carrying out the invention, those skilled in the art will appreciate that there are numerous variations, combinations, and permutations of the above described systems and methods. Based upon the above discussion and illustrations, those skilled in the art will readily recognize that various modifications and changes may be made to the various embodiments without strictly following the exemplary embodiments and applications illustrated and described herein. For example, although aspects and features may in some cases be described in individual figures, it will be appreciated that features from one figure can be combined with features of another figure even though the combination is not explicitly shown or explicitly described as a combination. Moreover, various specific features may be omitted and/or modified without departing from the invention. Thus, the reader should understand that the spirit and scope of the invention should be construed broadly as set forth in the appended claims.

What is claimed is:

1. An apparatus comprising:
    a display;
    a sensor configured and arranged to detect scattered or reflected light from a laser beam;
    at least one processor; and
    at least one memory storing computer-readable instructions that, when executed by the at least one processor, cause the processor to at least perform:
        receive, from the sensor, data associated with the laser light;
        process the data associated with the laser; and
        transmit an electronic signal configured to cause the display to provide visual representation of the laser light beam that includes a simulated projection the laser light beam in an augmented reality field of view of an operator, wherein the simulated projection of the laser light beam in the augmented reality field of view mimics an actual projection of the laser light beam the operator would view in a real life field of view without the display.

2. The apparatus of claim 1, further comprising a laser eye protection component and wherein the apparatus is a head-counted apparatus, and at least a portion of the laser eye protection component and at least a portion of the display are positioned to align with an eye region of a user.

3. The apparatus of claim 1, wherein the at least one memory further stores computer-readable instructions that, when executed by the at least one processor cause the apparatus to adjust a viewing position responsive to receiving a user selection to modify a viewing option.

4. The apparatus of claim 1, wherein the at least one memory further comprising computer-readable instructions that, when executed by the at least one processor, cause the processor to at least:
transmit an electronic signal configured to cause the optical display to output a graphical or textual information relating to a setting of the optical display.

5. The apparatus of claim 4, wherein the graphical or textual info cation comprises an indication of: a power meter output or a beam profile intensity measurement.

6. The apparatus of claim 1, wherein the at least one memory further comprises computer-readable instructions that, when executed by the at least one processor, cause the processor to at least:
transmit an electronic signal configured to output a plurality of user-selectable viewing options on the optical display.

7. The apparatus of claim 1, further comprising one or more input devices, and wherein the at least one memory further comprises computer-readable instructions that, when executed by the at least one processor, cause the processor to at least:
modify a setting of the optical display responsive to receiving a user selection via the one or more input devices.

8. A laser safety system comprising:
a head-mounted frame;
a sensor configured and arranged to detect scattered or reflected light from a laser light beam;
a safety lens module removably coupled to the head-mounted frame configured to be worn on a head of an operator and configured to block transmission of laser light; and
an optical display module removably coupled to the head-mounted frame and configured to receive data from the sensor and display a visual representation of the laser light beam that includes a simulated projection the laser light beam in an augmented reality field of view of the operator wearing the head-mounted frame, wherein the simulated projection of the laser light beam in the augmented reality field of view mimics an actual projection of the laser light beam the operator would view in a real life field of view without the optical display.

9. The system of claim 8, wherein the optical display module is configured to provide an augmented reality display including the visual representation of the laser light.

10. The system of claim 8, wherein the optical display module is configured to provide a plurality of user-selectable viewing options.

11. The system of claim 8, wherein the optical display module is configured to provide an indication of: a power meter output or a beam profile intensity measurement.

12. The system of claim 8, wherein the safety lens module includes a plurality of removable lens inserts, each lens insert rated for a specific laser wavelength.

13. The system of claim 8, wherein the head-mounted frame is configured to be worn with: only the safety lens module, only the optical display module, or both the safety lens module and the optical display module.

14. The apparatus of claim 8, wherein the simulated projection of the laser light beam is depicted in the same spatial location as the actual projection of the laser light beam.

* * * * *